US012624080B2

(12) United States Patent
Chen et al.

(10) Patent No.: US 12,624,080 B2
(45) Date of Patent: May 12, 2026

(54) MULTI-RECEPTOR (GLP-1 RECEPTOR, GIP RECEPTOR, AND Gcg RECEPTOR) AGONIST PROTEIN

(71) Applicant: Xintrum Pharmaceuticals, Ltd., Nanjing (CN)

(72) Inventors: Hai Chen, Nanjing (CN); Gaoyong Liao, Nanjing (CN); Yi Zhang, Nanjing (CN)

(73) Assignee: JIANGSU KANION PHARMACEUTICAL CO., LTD., Lianyungang (CN)

( * ) Notice: Subject to any disclaimer, the term of this patent is extended or adjusted under 35 U.S.C. 154(b) by 974 days.

(21) Appl. No.: 17/827,617

(22) Filed: May 27, 2022

(65) Prior Publication Data

US 2022/0298215 A1     Sep. 22, 2022

Related U.S. Application Data

(63) Continuation of application No. PCT/CN2021/131858, filed on Nov. 19, 2021.

(30) Foreign Application Priority Data

Dec. 10, 2020    (CN) .......................... 202011437400.0

(51) Int. Cl.
| | |
|---|---|
| *C07K 14/605* | (2006.01) |
| *A61P 3/04* | (2006.01) |
| *A61P 3/08* | (2006.01) |

(52) U.S. Cl.
CPC .............. *C07K 14/605* (2013.01); *A61P 3/04* (2018.01); *A61P 3/08* (2018.01)

(58) Field of Classification Search
None
See application file for complete search history.

(56) References Cited

FOREIGN PATENT DOCUMENTS

| | | |
|---|---|---|
| CN | 108271356 A | 7/2018 |
| CN | 109836504 A | 6/2019 |
| CN | 111944055 A | 11/2020 |
| WO | WO-2013192130 A1 * | 12/2013 ................ A61P 7/12 |

OTHER PUBLICATIONS

Machine translation of WO 2019101036, published May 31, 2019. (Year: 2019).*
STN CAS Registry, published Nov. 2008, p. 12 (Year: 2008).*
International Search Report on PCT/CN2021/131858.

* cited by examiner

*Primary Examiner* — Noble E Jarrell
(74) *Attorney, Agent, or Firm* — Yong Chen; Lin Sun-Hoffman; Liu Chen & Hoffman LLP

(57) ABSTRACT

This invention provides a novel protein. Experimental results have shown that the protein has agonist activity at three receptors, namely the glucagon-like peptide 1 (GLP-1) receptor, the glucose-dependent insulinotropic polypeptide (GIP) receptor, and the glucagon (Gcg) receptor, and has both blood glucose lowering and body weight reducing functions.

9 Claims, 3 Drawing Sheets

Specification includes a Sequence Listing.

MULTI-RECEPTOR (GLP-1 RECEPTOR, GIP RECEPTOR, AND Gcg RECEPTOR) AGONIST PROTEIN

TECHNICAL FIELD

The present invention relates to the field of biotechnology and more particularly to a multi-receptor agonist protein that is highly effective in reducing body weight and lowering blood glucose.

DESCRIPTION OF RELATED ART

As is well known in the art, glucagon-like peptide 1 (GLP-1), glucose-dependent insulinotropic polypeptide (GIP), and glucagon (Gcg) are all incretins related to metabolic disorders such as diabetes and obesity.

A glucagon-like peptide 1 receptor agonist (abbreviated as GLP-1RA) acts directly on the pancreas to promote the release of insulin and inhibit the secretion of glucagon. A GLP-1RA also inhibits peristalsis of the stomach, delays gastric emptying, and acts on the central nervous system to suppress appetite. Nevertheless, the foregoing treatment solutions have only limited therapeutic effects; their clinical therapeutic effects fail to satisfy the needs of a patient with a metabolic disorder completely.

By incorporating a plurality of metabolic pathways into a single treatment, however, multiple effects may be achieved to improve the existing therapeutic effects.

GIP is the major cause of the postprandial incretin effect in normal people and functions differently from GLP-1.

Gcg is a gastrointestinal hormone produced in the pancreas, increases blood glucose by stimulating gluconeogenesis and glycogenolysis in the liver, and enhances catabolism and thermogenesis.

In the prior art, drugs for treating diabetes and obesity have long been focused on those having an individual therapeutic effect on a single molecular target. Clinically, therefore, the use of concomitant drugs involves only a number of single-action drugs directed to their respective single targets, or a compound preparation of those drugs.

Studies have shown that administering a GLP-1RA together with a different gastrointestinal hormone can produce a synergistic effect. It is hence desirable to design and obtain a single molecule that has proper balanced activity at multiple receptors, or more particularly the GLP-1 receptor, the GIP receptor, and the Gcg receptor, in order to activate different signal pathways at the same time and thereby produce a synergistic effect on blood glucose control, body weight reduction, and regulation of the metabolism of body fat, the objective being to bring about such advantages as maximized therapeutic effects, reduced side effects, and stable pharmacokinetic properties.

BRIEF SUMMARY OF THE INVENTION

One objective of the present invention is to provide a protein that has agonist activity at three receptors—namely the GLP-1 receptor, the GIP receptor, and the Gcg receptor—at the same time, and that can reduce the body weight and lower the blood glucose of a patient with diabetes significantly.

The present invention provides a multi-receptor agonist protein (hereinafter also referred to as GGGF1 for short) having the amino acid sequence of SEQ ID NO: 2.

Sites 1-39 of the amino acid sequence of the protein GGGF1 constitute an active functional area and have the amino acid sequence of SEQ ID NO: 1, whereas the remaining portion of the amino acid sequence makes up a non-functional area and serves to increase protein stability.

The multi-receptor agonist protein exists in the form of a homodimer.

The present invention involves constructing the multi-receptor agonist protein in an expression vector, wherein the expression vector is a eukaryotic expression vector and can be introduced into a host cell by transient transfection or stable transfection.

The host cell is a mammalian cell, and the mammalian cell is a Chinese hamster ovary (CHO) cell or a human embryonic kidney 293 cell.

More specifically, the following research work was conducted for the present invention:

1. A nucleotide sequence corresponding to the amino acid sequence of GGGF1 was designed and synthesized in accordance with the codon usage bias of the CHO cell and was constructed in the pcDNA3.4 vector to produce the expression vector pcDNA3.4-GGGF1.

2. The expression vector was transfected into a CHO cell through a transfection reagent, and after culturing, a cell supernatant in which GGGF1 was expressed was obtained.

3. GGGF1 was separated and purified through Protein A and was tested by sodium dodecyl sulfate-polyacrylamide gel electrophoresis (SDS-PAGE).

4. The bioactivity of GGGF1 was tested with the GLP-1 receptor, the GIP receptor, and the Gcg receptor.

5. A study on the activity of GGGF1 in reducing body weight and lowering blood glucose was conducted on db/db diabetic model mice.

The results of multiple experiments have proved that the protein provided by the present invention can:

1. Activate multiple receptors, namely the GLP-1, GIP, and Gcg receptors, simultaneously (see embodiments 2, 3, and 4);

2. Reduce body weight significantly ($P<0.05$) (see embodiment 5);

3. Lower the non-fasting blood glucose (NFBG) level ($P<0.001$) and the fasting blood glucose (FBG) level ($P<0.0001$) extremely significantly (see embodiment 5); and 4. Lower the glycated hemoglobin (HbA1c) level significantly ($P<0.01$) (see embodiment 5).

SEQUENCE LISTING INFORMATION

SEQ ID NO: 1: Amino acid sequence of the functional area of the protein GGGF1;

SEQ ID NO: 2: Amino acid sequence of the protein GGGF1.

DETAILED DESCRIPTION OF THE INVENTION

As mentioned in connection with the following embodiments, "Dul" refers to Dulaglutide, a blood glucose lowering drug that was made by Eli Lilly and Company and was purchased for use in the control group.

Embodiment 1: Preparation of the Multi-Receptor Agonist Protein GGGF1

1. Construction of an Expression Vector for the Multi-Receptor Agonist Protein

Based on the features of CHO cell expression, the amino acid sequence of GGGF1 was optimized and reverse-translated into a nucleotide sequence, which was then synthesized chemically, digested with the restriction enzymes EcoRI and BamHI, and purified with a gel extraction kit to produce enzymatically digested DNA fragments. The pcDNA3.4 vector was digested with the same two restriction enzymes EcoRI and BamHI, and the enzymatic digestion product was purified with a DNA purification kit.

Figure 1:
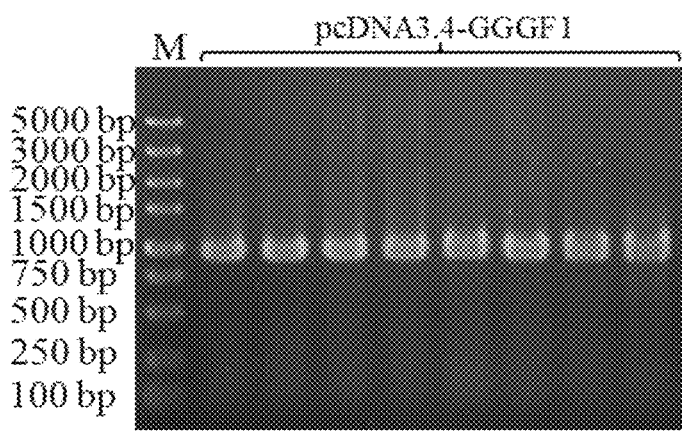
FIG. 1: The result of agarose gel electrophoresis of a positive clone of the constructed and polymerase chain reaction (PCR)-screened GGGF1 expression vector pcDNA3.4-GGGF1.

Using the T4 DNA ligase, the GGGF1 gene that had been digested with EcoRI and BamHI was ligated to the pcDNA3.4 vector that had been digested with the same two enzymes, and the ligated insert and vector were chemically transformed into a Top10 competent cell. The single colony that grew after the transformation was screened by PCR in order to obtain positive clones. The size of a PCR product in which the target gene had been successfully ligated to the expression vector was about 900-1000 bp, and FIG. 1 shows the result of agarose gel electrophoresis of such a PCR product.

Some of the PCR-screened positive clones pcDNA3.4-GGGF1 were selected for sequencing, and a comparison and analysis of the sequence obtained revealed that the nucleotide sequence of GGGF1 was consistent with the theoretical sequence.

2. Expression of the Multi-Receptor Agonist Protein

Figure 2:
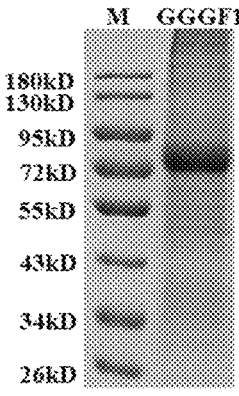
FIG. 2: The result of non-reduced SDS-PAGE of a GGGF1-expressed supernatant.

The host cells (CHO cells) were cultured under the following conditions: A culture medium designed for CHO cell expression was used, the orbital shaker had an orbit diameter of 2.5 cm and a rotation speed of 120 rpm, the carbon dioxide concentration was 8%, and the temperature was 37° C. Subculturing was performed when the cell count of the CHO cells reached $4\text{-}6\times10^6$ cells/mL, and the cell density in the subcultures was adjusted to $2\text{-}5\times10^5$ cells/mL. The day before transfection, the cells were subcultured again, and the cell density was adjusted to $3\text{-}4\times10^5$ cells/mL. Prior to transfection, the cell density was adjusted with a complete culture medium to $6\times10^6$ cells/mL. An appropriate transfection volume was chosen according to the purpose of the experiment. In a 1.5-mL centrifuge tube, the expression vector pcDNA3.4-GGGF1 in Step 1 was added, after being purified, at a ratio of 0.133 μg per $10^6$ to-be-transfected cells, and then optiPRO SFM was added until a final volume of 6.7 μL per $10^6$ to-be-transfected cells was reached. After that, the centrifuge tube was shaken at a moderate speed until its contents were thoroughly mixed. In another 1.5-mL centrifuge tube, two reagents, namely ExpiFectamine CHO Reagent (a transfection reagent) and optiPRO SFM, were added at a ratio of 0.533 μL per $10^6$ cells and a ratio of 6.134 μL per $10^6$ cells respectively, and the centrifuge tube was shaken at a moderate speed until its contents were thoroughly mixed. Immediately after that, the diluted transfection reagent was mixed with the vector solution, and the mixture was placed at room temperature for 1-5 min. The vector-transfection reagent mixture solution was then added into the cell suspension by drops, and the resulting mixture was transferred at once to a 37° C., 8% $CO_2$ shaker for culturing. After 20 hours of culture, an enhancer and a feed were added into the shaker flask at a ratio of 1 μL per $10^6$ to-be-transfected cells and a ratio of 40 μL per $10^6$ to-be-transfected cells respectively, and the culture conditions were adjusted to 32° C. and 5% $CO_2$. On the 9th day of culture, the culture supernatant was collected by centrifugation and kept at a temperature not higher than −70° C. Samples were then taken for non-reduced SDS-PAGE, whose result is shown in FIG. 2, indicating that GGGF1 was successfully expressed.

3. Separation and Purification of the Multi-Receptor Agonist Protein

Figure 3:
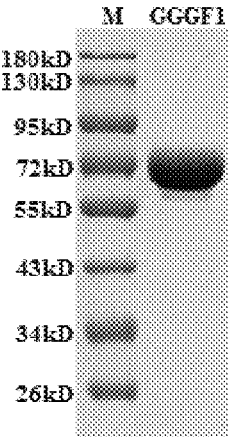
FIG. 3: The result of non-reduced SDS-PAGE of Protein A-purified GGGF1.

The GGGF1-expressed supernatant in Step 2 was separated and purified with the Protein A filler. Phosphate-buffered saline (PBS) was used as the equilibrium buffer, and a pH3.0, 100 mM citric acid/sodium citrate buffer as the elution buffer. The eluate corresponding to the elution peak was collected and substituted into the PBS buffer to obtain the protein GGGF1. The protein content was determined by the ultraviolet method. The result of non-reduced SDS-PAGE is shown in FIG. 3.

Embodiment 2: Experiment on the Agonist Activity of the Protein GGGF1 at the GLP-1 Receptor The method employed and its principle:

The bioactivity of the multi-receptor agonist protein GGGF1 was determined by the luciferase reporter gene method. The cell HEK293-GLP1R-CRE-Luc can express the GLP-1 receptor stably, with CRE specifically promoting expression of the luciferase, and this signal pathway can be specifically promoted by the cell HEK293-GLP1R-CRE-Luc binding to the GLP-1 receptor after being treated with the multi-receptor agonist protein. As the last step, therefore, a substrate is added to produce a chemiluminescent signal, whose intensity is positively correlated to the bioactivity of the multi-receptor agonist protein.

The steps of the method are as follows:

Poly-L-lysine was added to a 96-hole plate at a concentration of 0.1 mg/mL and in an amount of 100 μL per hole, and the hole walls were allowed to be coated with the poly-L-lysine at 37° C. for 24 h. Before use, the plate was washed once with sterile double-distilled water and then put into an incubator in order for the water to evaporate. After that, the 96-hole plate was inoculated with the cell HEK293-GLP1R-CRE-Luc at a cell density of $3\times10^4$/hole, and the number of the holes to be inoculated was determined according to the number of the samples to be tested. Each drug was applied to 3 columns×9 rows of cells. The protein GGGF1 was diluted to the concentrations of 10, 2, 0.4, 0.08, 0.016, 0.0032, 0.00064, 0.000128, and 0 nM. Dulaglutide (or Dul for short), which is made by Eli Lilly and Company and commercially available, was used in the control group and was diluted to produce the same concentration gradient. The culture solution in each hole was discarded, before 100 μL of diluted GGGF1 solution was added to each hole. After 24 hours of culture, the 96-hole plate was taken out of the incubator, and 100 μL of One-Glo Luciferase Assay solution, which was prepared in advance and had been brought to room temperature, was added to each hole, thoroughly mixed, and allowed to rest for 5 min in order for lysis to take place. The numerical values of each hole were determined with a multifunctional microplate reader by the chemiluminescence method. The chemiluminescence value-concentration curve of each fusion protein was fitted with the software GraphPad Prism (using the three-parameter nonlinear regression equation fitting mode). The $EC_{50}$ value, which can be used to indicate the bioactivity of GGGF1, was subsequently calculated.

The experimental results are shown in Table 1.

Conclusion of the experiment: Both the protein GGGF1 of the present invention and Dulaglutide (Dul) were able to bind to the GLP-1 receptor.

Embodiment 3: Experiment on the Agonist Activity of the Protein GGGF1 at the GIP Receptor The method employed and its principle:

The bioactivity of the multi-receptor agonist protein GGGF1 in activating the GIP receptor was determined with CHO-K1-GIPR, which is a cell strain capable of overexpression of the GIP receptor, and the underlying principle is as follows. When the multi-receptor agonist protein has reacted with the cell CHO-K1-GIPR for a while, the cyclic adenosine monophosphate (cAMP) content of the cell will have increased, and the cAMP content is positively correlated to the activity of the drug within a certain range. Therefore, the bioactivity of the drug/agonist to be tested can be known by measuring how the cAMP signal in the cell varies with the concentration of the drug. In this experiment, the bioactivity of the multi-receptor agonist protein in activating the GIP receptor was determined by a method entailing competition between externally marked cAMP and the cAMP produced.

The steps of the method are as follows:

Well-grown CHO-K1-GIPR cells were selected, digested with pancreatin, washed twice with Dulbecco's phosphate-buffered saline (DPBS), resuspended with a 1× stimulation buffer, and counted. The cell density was then adjusted to $6\times10^5$ cells/mL. Each hole of a 96-hole plate was added with 5 µL of the cell suspension, followed by 5 µL of the to-be-tested drug GGGF1 at a corresponding concentration, which started with the highest concentration of 200 nM and was sequentially reduced by 5 times gradient dilution. Dulaglutide (Dul), which is made by Eli Lilly and Company and commercially available, was used in the control group and was diluted to produce the same concentration gradient. Also, a cAMP standard area was established, in which each hole was added with 5 µL of cAMP at a corresponding concentration. The 96-hole plate was covered with a sealing film and placed in an incubator for incubation at 37° C. for 30 min. Following that, the 96-hole plate was taken out of the incubator, and each hole was added with 5 µL of a cAMP working fluid. After a thorough mix, each hole was further added with 5 µL of an anti-cAMP-cryptate working fluid. After another thorough mix, the plate was covered with a sealing film again, allowing incubation to take place at room temperature for 1 hour. The ratio values of (signal 665 nm/signal 620 nm)*10000 were read from a multifunctional microplate reader, and data processing and analysis was carried out with the software GraphPad Prism6. The $EC_{50}$ value of the drug under test, i.e., GGGF1, was subsequently calculated.

The experimental results are shown in Table 1.

Conclusion of the experiment: The protein GGGF1 of the present invention was able to bind to the GIP receptor, whereas Dulaglutide (Dul) and the GIP receptor produced no binding signal.

Embodiment 4: Experiment on the Agonist Activity of the Protein GGGF1 at the Gcg Receptor The method employed and its principle:

The bioactivity of the multi-receptor agonist protein GGGF1 in activating the Gcg receptor was determined with CHO-K1-GcgR, which is a cell strain capable of overexpression of the Gcg receptor, and the underlying principle is as follows. When the multi-receptor agonist protein has reacted with the cell CHO-K1-GcgR for a while, the cAMP content of the cell will have increased, and the cAMP content is positively correlated to the activity of the drug within a certain range. Therefore, the bioactivity of the drug/agonist to be tested can be known by measuring how the cAMP signal in the cell varies with the concentration of the drug. In this experiment, the bioactivity of the multi-receptor agonist protein in activating GcgR (i.e., the Gcg receptor) was determined by a method entailing competition between externally marked cAMP and the cAMP produced.

The steps of the method are as follows:

Well-grown CHO-K1-GcgR cells were selected, digested with pancreatin, washed twice with DPBS, resuspended with a 1× stimulation buffer, and counted. The cell density was then adjusted to $6\times10^5$ cells/mL. Each hole of a 96-hole plate was added with 5 µL of the cell suspension, followed by 5 µL of the to-be-tested drug GGGF1 at a corresponding concentration, which started with the highest concentration of 10000 nM and was sequentially reduced by 10 times gradient dilution. Dulaglutide (Dul), which is made by Eli Lilly and Company and commercially available, was used in the control group and was diluted to produce the same concentration gradient. Also, a cAMP standard area was established, in which each hole was added with 5 µL of cAMP at a corresponding concentration. The 96-hole plate was covered with a sealing film and placed in an incubator for incubation at 37° C. for 30 min Following that, the 96-hole plate was taken out of the incubator, and each hole was added with 5 µL of a cAMP working fluid. After a thorough mix, each hole was further added with 5 µL of an anti-cAMP-cryptate working fluid. After another thorough mix, the plate was covered with a sealing film again, allowing incubation to take place at room temperature for 1 hour. The ratio values of (signal 665 nm/signal 620 nm)*10000 were read from a multifunctional microplate reader, and data processing and analysis was carried out with the software GraphPad Prism6. The $EC_{50}$ value of the drug under test, i.e., GGGF1, was subsequently calculated.

The experimental results are shown in Table 1.

Conclusion of the experiment: The protein GGGF1 of the present invention was able to bind to the Gcg receptor, whereas Dulaglutide (Dul) and the Gcg receptor produced no binding signal.

TABLE 1

| Comparison of bioactivity in binding to three receptors ($EC_{50}$ values) | | | |
|---|---|---|---|
| Sample name | GLP-1 receptor | GIP receptor | Gcg receptor |
| GGGF1 | 0.01876 nM | 5.521 nM | 0.1003 nM |
| Dul | 0.0237 nM | No signal | No signal |

Overall Conclusion of the Experiments:

The experimental results of binding the protein GGGF1 of the present invention to three incretins that are related to diabetes and obesity, namely the GLP-1 receptor, the GIP receptor, and the Gcg receptor, have proved the following:

1. The protein GGGF1 of the present invention can bind to the three receptors (i.e., the GLP-1, GIP, and Gcg receptors) at the same time;

2. The commercially available blood glucose lowering drug in the control group, i.e., Dulaglutide (Dul), can bind only to the GLP-1 receptor; and 3. GGGF1 has higher affinity to the GLP-1 receptor than Dul, and this implies that GGGF1 may be more effective than Dul in reducing body weight and lowering blood glucose.

Embodiment 5: Investigation on the Activity of the Multi-Receptor Agonist Protein GGGF1 in Reducing the Body Weight, and Lowering the Blood Glucose, of db/db Diabetic Model Mice Purpose of the experiment: To investigate the body weight reducing and blood glucose lowering activity of the multi-receptor agonist protein GGGF1 in db/db type-2 diabetic model mice.

Experimental Animals and their Grouping:

24 db/db male mice were chosen for the experiment. The mice were 6 weeks old when received and underwent adaptive feeding in an animal house for 1 week. After the week, blood was drawn from the tail tip for an NFBG test. After fasting for 6 hours, blood was drawn from the tail tip again for an FBG test, and 50 μL of blood was drawn from the retrobulbar venous plexus and subjected to whole blood separation in order to perform an HbA1c test on the plasma obtained.

The experimental animals were randomly divided into three groups according primarily to the FBG level and secondarily to body weight. The three groups were the model group (i.e., the blank control group, or vehicle group, with n=8), the positive control group (i.e., the Dul group, in which the commercially available Dulaglutide, made by Eli Lilly and Company, was used), with n=8), and the GGGF1 administration group (i.e., the GGGF1 group, with n=8).

Method of the Experiment:

8

Every three days, the GGGF1 administration group and the positive control group were given their respective drugs through subcutaneous injection over the neck at 16.67 nmol/kg.

The vehicle group was given a placebo.

Prior to drug administration, blood was drawn from the tail tip in order to perform an NFBG test. After fasting for 6 hours, an FBG test was conducted, and the body weight taken. The drugs were administered continuously for 16 times. On the 3rd day after the last drug administration, the mice were fasted for 6 hours before their body weight was taken and their FBG and HbA1c tested.

Experimental Results:

FIG. 4 to FIG. 7 sequentially show the experimental results of the body weight reducing and blood glucose lowering effects of the protein GGGF1.

Figure 4:
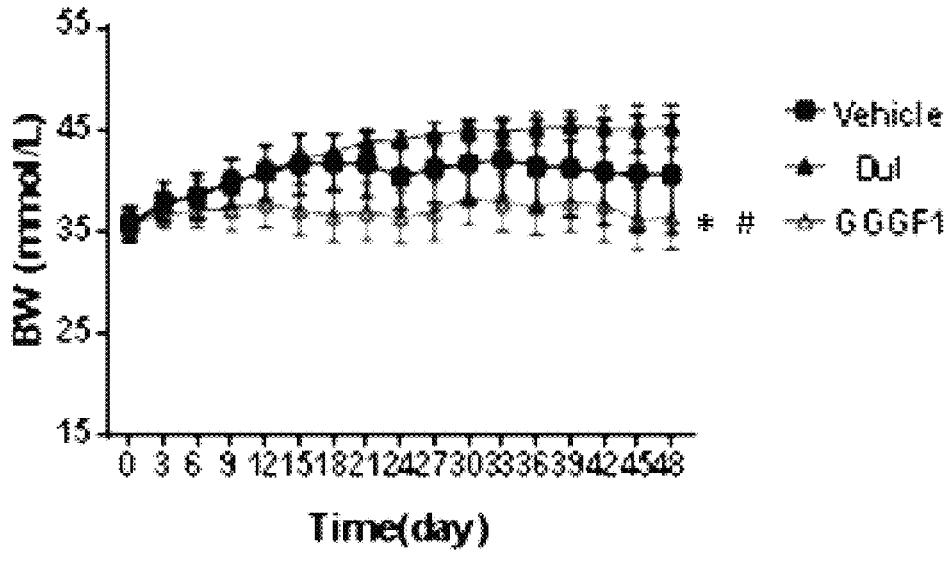
FIG. 4: The body weight reducing effect of the protein GGGF1 on db/db diabetic model mice.
Figure 5:
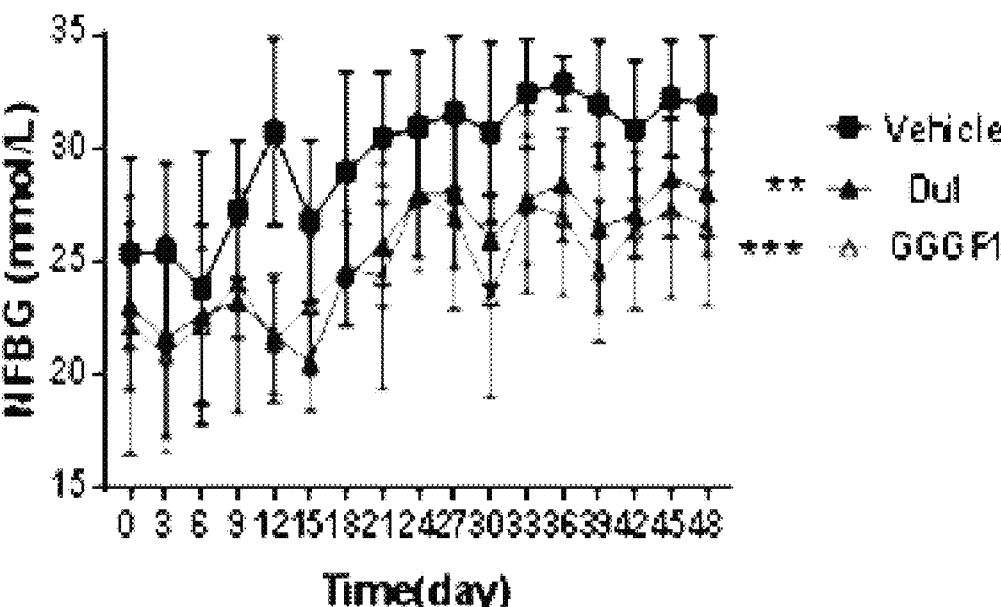
FIG. 5: The NFBG level lowering effect of the protein GGGF1 on db/db diabetic model mice.
Figure 6:
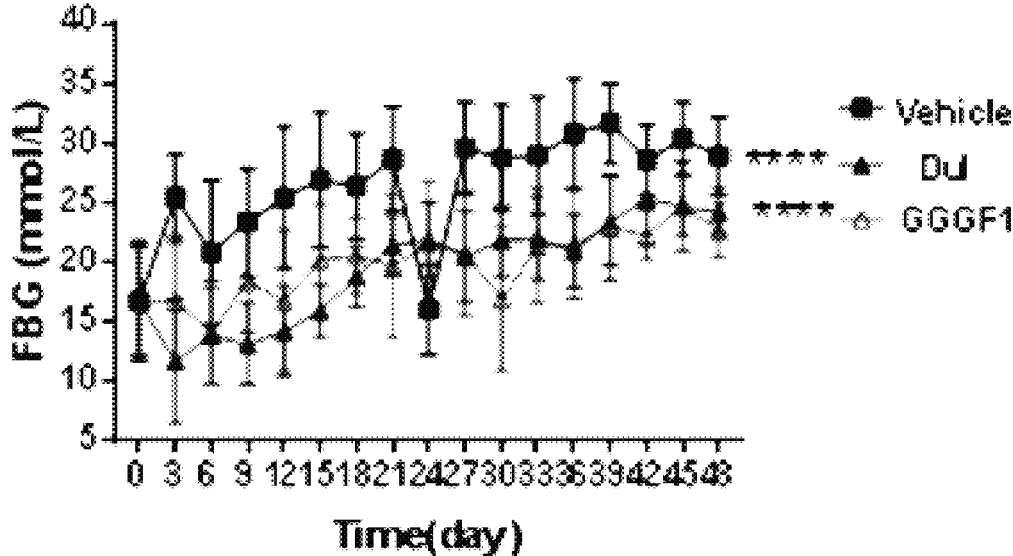
FIG. 6: The FBG level lowering effect of the protein GGGF1 on db/db diabetic model mice.

More specifically,

FIG. 4 shows the body weight reducing effect on the db/db diabetic model mice;

FIG. 5 shows the NFBG lowering effect;

FIG. 6 shows the FBG lowering effect; and

Figure 7:
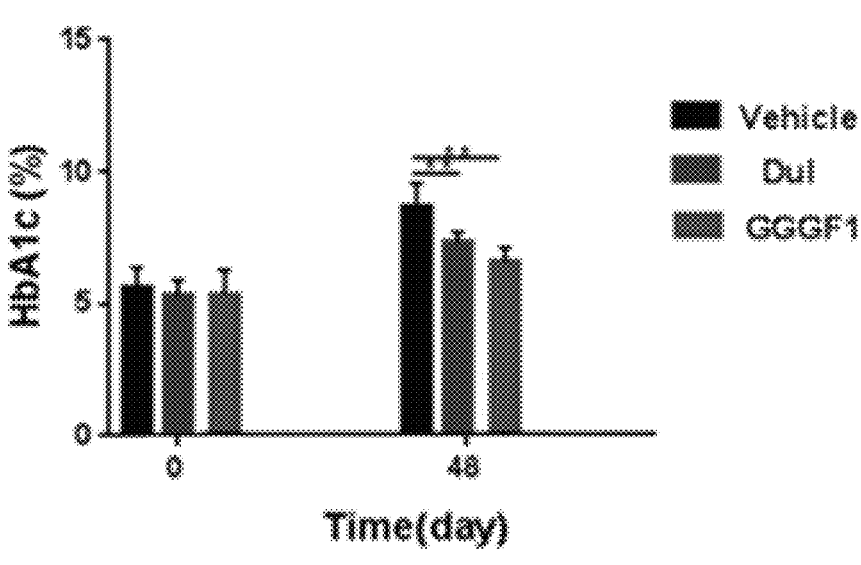
FIG. 7: The HbA1c level lowering effect of the protein GGGF1 on db/db diabetic model mice.

FIG. 7 shows the HbA1c level lowering effect.

The following can be known from the experimental results:

1. GGGF1 had the following effects in comparison with the vehicle group (i.e., the blank control group, to which no drug was administered):

1) Reducing body weight significantly (*, $P<0.05$);

2) Lowering the NFBG level extremely significantly (***, $P<0.001$);

3) Lowering the FBG level extremely significantly (****, $P<0.0001$); and

4) Lowering the HbA1c level significantly (**, $P<0.01$).

2. Compared with the positive drug Dul (Dulaglutide) control group, GGGF1 was more effective in lowering NFBG.

Conclusion of the Experiment

The animal experiment shows that the protein GGGF1 of the present invention has both a blood glucose lowering function and a body weight reducing function.

The invention claimed is:

1. A protein consisting of the amino acid sequence of SEQ ID NO:1 or SEQ ID NO:2.

2. A body weight reducing agent comprising the protein of claim 1.

3. A method of reducing body weight of a subject, comprising administering to the subject the protein of claim 1.

4. A blood glucose lowering agent comprising the protein of claim 1.

5. A protein consisting of the amino acid sequence of SEQ ID NO:1.

6. A protein consisting of the amino acid sequence of SEQ ID NO:2.

7. The protein of claim 1, where the protein is an agonist for the glucagon-like peptide 1 (GLP-1) receptor.

8. The protein of claim 1, where the protein is an agonist for the glucose-dependent insulinotropic polypeptide (GIP) receptor.

9. The protein of claim 1, where the protein is an agonist for the glucagon (Geg) receptor.

* * * * *

SEQUENCE LISTING

```
<160> NUMBER OF SEQ ID NOS: 2

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

His Ser Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 2
<211> LENGTH: 283
<212> TYPE: PRT
<213> ORGANISM: Artificial Sequence
<220> FEATURE:
<223> OTHER INFORMATION: Synthetic
```

```
<400> SEQUENCE: 2

His Ser Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
                20                  25                  30

Ser Gly Ala Pro Pro Pro Ser Gly Gly Gly Gly Ser Gly Gly Gly Gly
            35              40                  45

Ser Gly Gly Gly Gly Ser Ala Glu Ser Lys Tyr Gly Pro Pro Cys Pro
    50                  55                  60

Pro Cys Pro Ala Pro Glu Ala Ala Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser Gln Glu Asp Pro Glu Val Gln Phe
                100                 105                 110

Asn Trp Tyr Val Asp Gly Val Glu Val His Asn Ala Lys Thr Lys Pro
            115                 120                 125

Arg Glu Glu Gln Phe Asn Ser Thr Tyr Arg Val Val Ser Val Leu Thr
    130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175

Lys Gly Gln Pro Arg Glu Pro Gln Val Tyr Thr Leu Pro Pro Ser Gln
                180                 185                 190

Glu Glu Met Thr Lys Asn Gln Val Ser Leu Thr Cys Leu Val Lys Gly
            195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
                260                 265                 270

Tyr Thr Gln Lys Ser Leu Ser Leu Ser Leu Gly
                275                 280
```